United States Patent
Stoddard et al.

(10) Patent No.: US 9,265,847 B2
(45) Date of Patent: Feb. 23, 2016

(54) PROCESS OF COOLING SURGICAL DEVICE BATTERY BEFORE OR DURING HIGH TEMPERATURE STERILIZATION

(71) Applicant: COVIDIEN LP, Mansfield, MA (US)

(72) Inventors: Robert B. Stoddard, Steamboat Springs, CO (US); James S. Cunningham, Boulder, CO (US); William J. Dickhans, Longmont, CO (US); Russell D. Hempstead, Lafayette, CO (US); Eric R. Larson, Boulder, CO (US); Duane E. Kerr, Loveland, CO (US); William H. Nau, Jr., Longmont, CO (US); Anthony B. Ross, Boulder, CO (US); John J. Kappus, Denver, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/806,315

(22) Filed: Jul. 22, 2015

(65) Prior Publication Data

US 2015/0335772 A1 Nov. 26, 2015

Related U.S. Application Data

(62) Division of application No. 13/436,107, filed on Mar. 30, 2012, now Pat. No. 9,114,181.

(60) Provisional application No. 61/469,543, filed on Mar. 30, 2011.

(51) Int. Cl.
*H01M 10/50* (2006.01)
*H02J 7/00* (2006.01)
*A61L 2/00* (2006.01)
*A61L 2/07* (2006.01)

(52) U.S. Cl.
CPC ............... *A61L 2/07* (2013.01); *H02J 7/0013* (2013.01); *H02J 7/0057* (2013.01)

(58) Field of Classification Search
CPC .......................................................... A61L 2/07
USPC .......... 320/107, 112; 429/62; 422/1, 109, 307
See application file for complete search history.

(56) References Cited

U.S. PATENT DOCUMENTS

| | | | |
|---|---|---|---|
| 4,641,076 A | * | 2/1987 | Linden ............... A61L 2/00 320/113 |
| 5,013,993 A | | 5/1991 | Bhagwat et al. |
| 5,204,609 A | | 4/1993 | Alisauski |
| 5,229,703 A | | 7/1993 | Harris |
| 5,293,109 A | | 3/1994 | Fischl et al. |
| 5,296,797 A | | 3/1994 | Bartlett |

(Continued)

FOREIGN PATENT DOCUMENTS

| | | |
|---|---|---|
| JP | 2000237204 A | 9/2000 |
| WO | 0054682 A1 | 9/2000 |
| WO | 02/085218 A2 | 10/2002 |

*Primary Examiner* — Richard V Muralidar

(57) ABSTRACT

A dual-mode autoclave for sterilizing a battery is disclosed including a controller and an environmental system in operative communication with the controller and configured sterilize a battery contained within the dual-mode autoclave in response to a command from the controller. The environmental system configured to reduce a temperature of the battery to a first, pre-cooled temperature during a first operational phase and configured to increase the temperature of the battery to a second, autoclaving temperature during a second operational phase.

18 Claims, 4 Drawing Sheets

(56) References Cited

U.S. PATENT DOCUMENTS

| | | |
|---|---|---|
| 5,346,502 A | 9/1994 | Estabrook et al. |
| 5,463,305 A | 10/1995 | Koenck |
| 5,504,416 A | 4/1996 | Holloway et al. |
| 5,561,359 A | 10/1996 | Matsuura et al. |
| 5,583,418 A | 12/1996 | Honda et al. |
| 5,608,306 A | 3/1997 | Rybeck et al. |
| 5,617,005 A | 4/1997 | Brown, Jr. et al. |
| 5,617,006 A | 4/1997 | Lenhart et al. |
| 5,623,194 A | 4/1997 | Boll et al. |
| 5,647,450 A | 7/1997 | Ogawa et al. |
| 5,696,435 A | 12/1997 | Koenck |
| 5,703,471 A | 12/1997 | Bullock et al. |
| 5,717,306 A | 2/1998 | Shipp |
| 5,773,962 A | 6/1998 | Nor |
| 5,776,155 A | 7/1998 | Beaupre et al. |
| 5,810,859 A | 9/1998 | DiMatteo et al. |
| 5,811,959 A | 9/1998 | Kejha |
| 5,847,543 A | 12/1998 | Carroll |
| 5,864,224 A | 1/1999 | Takechi et al. |
| 5,873,873 A | 2/1999 | Smith et al. |
| 5,874,825 A | 2/1999 | Brotto |
| 5,896,024 A | 4/1999 | Bradus et al. |
| 5,897,569 A | 4/1999 | Kellogg et al. |
| 5,944,737 A | 8/1999 | Tsonton et al. |
| 5,968,060 A | 10/1999 | Kellogg |
| 5,980,510 A | 11/1999 | Tsonton et al. |
| 5,982,152 A | 11/1999 | Watanabe et al. |
| 5,989,275 A | 11/1999 | Estabrook et al. |
| 6,018,227 A | 1/2000 | Kumar et al. |
| 6,020,721 A | 2/2000 | Brotto |
| 6,051,010 A | 4/2000 | DiMatteo et al. |
| 6,061,551 A | 5/2000 | Sorrells et al. |
| 6,063,098 A | 5/2000 | Houser et al. |
| 6,068,647 A | 5/2000 | Witt et al. |
| 6,154,008 A | 11/2000 | Bradus et al. |
| 6,160,376 A | 12/2000 | Kumar et al. |
| 6,184,656 B1 | 2/2001 | Karunasiri et al. |
| 6,191,501 B1 | 2/2001 | Bos |
| 6,218,807 B1 | 4/2001 | Sakaue et al. |
| 6,225,780 B1 | 5/2001 | Koch |
| 6,225,788 B1 | 5/2001 | Kouzu et al. |
| 6,239,044 B1 | 5/2001 | Kashiwagi et al. |
| 6,251,110 B1 | 6/2001 | Wampler |
| 6,257,241 B1 | 7/2001 | Wampler |
| 6,274,963 B1 | 8/2001 | Estabrook et al. |
| 6,287,344 B1 | 9/2001 | Wampler et al. |
| 6,331,761 B1 | 12/2001 | Kumar et al. |
| 6,344,728 B1 | 2/2002 | Kouzu et al. |
| 6,411,063 B1 | 6/2002 | Kouzu et al. |
| 6,425,906 B1 | 7/2002 | Young et al. |
| 6,425,912 B1 | 7/2002 | Knowlton |
| 6,455,186 B1 | 9/2002 | Moores, Jr. et al. |
| 6,462,513 B1 | 10/2002 | Bradus et al. |
| 6,491,708 B2 | 12/2002 | Madan et al. |
| 6,514,249 B1 | 2/2003 | Maguire et al. |
| 6,541,780 B1 | 4/2003 | Richards et al. |
| 6,547,788 B1 | 4/2003 | Maguire et al. |
| 6,577,883 B1 | 6/2003 | Ueda |
| 6,731,096 B1 | 5/2004 | Patino et al. |
| 6,756,766 B2 | 6/2004 | Miller |
| 6,847,190 B2 * | 1/2005 | Schaefer .................. A61L 2/07 320/107 |
| 6,869,431 B2 | 3/2005 | Maguire et al. |
| 7,014,945 B2 | 3/2006 | Moores, Jr. et al. |
| 7,056,616 B2 | 6/2006 | Moores, Jr. et al. |
| 7,059,769 B1 | 6/2006 | Potega |
| 7,061,246 B2 | 6/2006 | Dougherty et al. |
| 7,135,029 B2 | 11/2006 | Makin et al. |
| 7,248,017 B2 | 7/2007 | Cheng et al. |
| 7,252,904 B2 | 8/2007 | Moores, Jr. et al. |
| 7,270,656 B2 | 9/2007 | Gowda et al. |
| 7,275,440 B2 | 10/2007 | Gunnerman et al. |
| 7,326,490 B2 | 2/2008 | Moores, Jr. et al. |
| 7,372,237 B2 | 5/2008 | Bushong et al. |
| 7,474,228 B2 | 1/2009 | Lockhart et al. |
| 7,528,571 B2 | 5/2009 | Kernahan et al. |
| 7,530,986 B2 | 5/2009 | Beaupre et al. |
| 7,533,830 B1 | 5/2009 | Rose |
| 7,559,241 B2 | 7/2009 | Gunnerman |
| 7,572,549 B2 | 8/2009 | Wegner |
| 7,592,776 B2 | 9/2009 | Tsukamoto et al. |
| 7,705,559 B2 * | 4/2010 | Powell .................. H02J 7/0042 320/113 |
| 7,872,446 B2 * | 1/2011 | Cover ................. A61B 1/00034 307/150 |
| 8,344,690 B2 * | 1/2013 | Smith ....................... A61L 2/00 320/108 |
| 8,444,664 B2 | 5/2013 | Balanev et al. |
| 8,662,745 B2 | 3/2014 | Misuchenko et al. |
| 9,114,181 B2 * | 8/2015 | Stoddard ................... A61L 2/07 |
| 2003/0114874 A1 | 6/2003 | Craig et al. |
| 2005/0049546 A1 | 3/2005 | Messerly et al. |
| 2005/0258802 A1 * | 11/2005 | Dickinson ................. H01M 2/36 320/112 |
| 2007/0018610 A1 | 1/2007 | Wegner |
| 2007/0173746 A1 | 7/2007 | Barzilay et al. |
| 2007/0182369 A1 | 8/2007 | Gerber et al. |
| 2007/0225618 A1 | 9/2007 | Ward et al. |
| 2007/0244471 A1 | 10/2007 | Malackowski |
| 2007/0268001 A1 | 11/2007 | Doll et al. |
| 2008/0191666 A1 | 8/2008 | Kernahan et al. |
| 2008/0191667 A1 | 8/2008 | Kernahan et al. |
| 2008/0234709 A1 | 9/2008 | Houser |
| 2008/0234710 A1 | 9/2008 | Neurohr et al. |
| 2008/0284372 A1 | 11/2008 | Cover et al. |
| 2009/0030437 A1 | 1/2009 | Houser et al. |
| 2009/0036913 A1 | 2/2009 | Wiener et al. |
| 2009/0036914 A1 | 2/2009 | Houser |
| 2009/0143795 A1 | 6/2009 | Robertson |
| 2009/0149797 A1 | 6/2009 | Dacey, Jr. et al. |
| 2009/0149798 A1 | 6/2009 | Dacey, Jr. et al. |
| 2009/0177218 A1 | 7/2009 | Young et al. |
| 2009/0177219 A1 | 7/2009 | Conlon |
| 2009/0209900 A1 | 8/2009 | Carmeli et al. |
| 2011/0241786 A1 | 10/2011 | Gilbert |
| 2012/0253328 A1 | 10/2012 | Cunningham et al. |
| 2012/0310229 A1 | 12/2012 | Gregg |
| 2013/0030328 A1 | 1/2013 | Dycus et al. |
| 2013/0085419 A1 | 4/2013 | Stoddard et al. |
| 2013/0197511 A1 | 8/2013 | Balanev et al. |
| 2014/0017118 A1 | 1/2014 | Stoddard et al. |

* cited by examiner

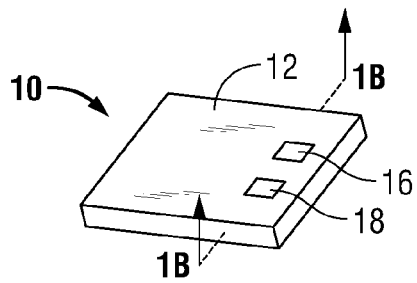
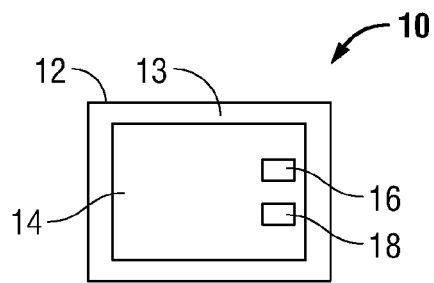
FIG. 1A  FIG. 1B
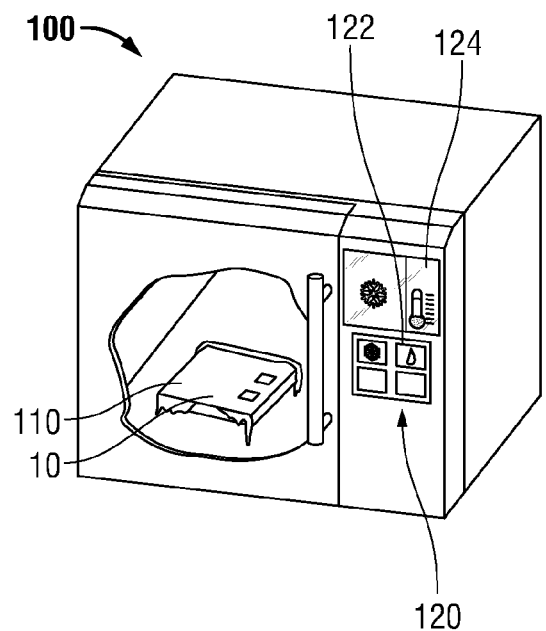
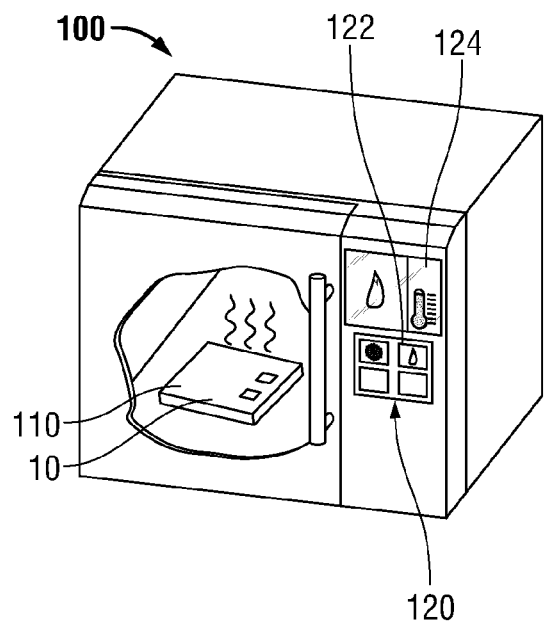
FIG. 2  FIG. 3

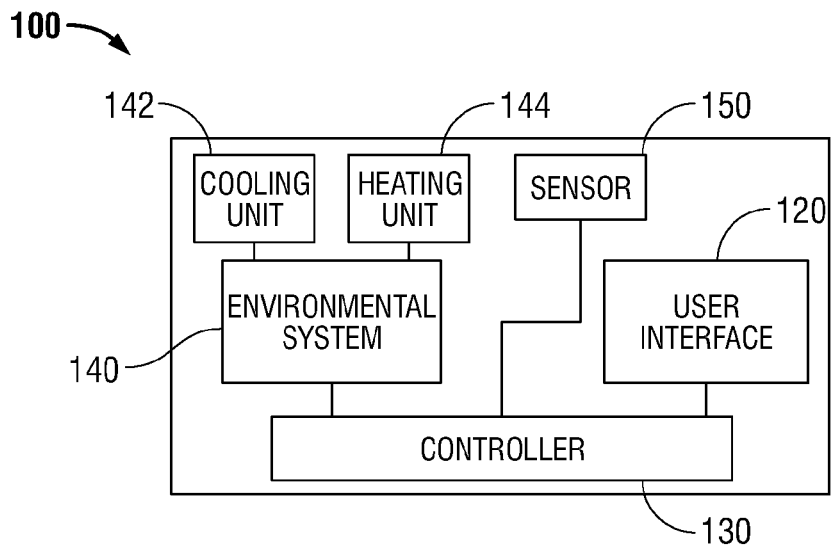
FIG. 4
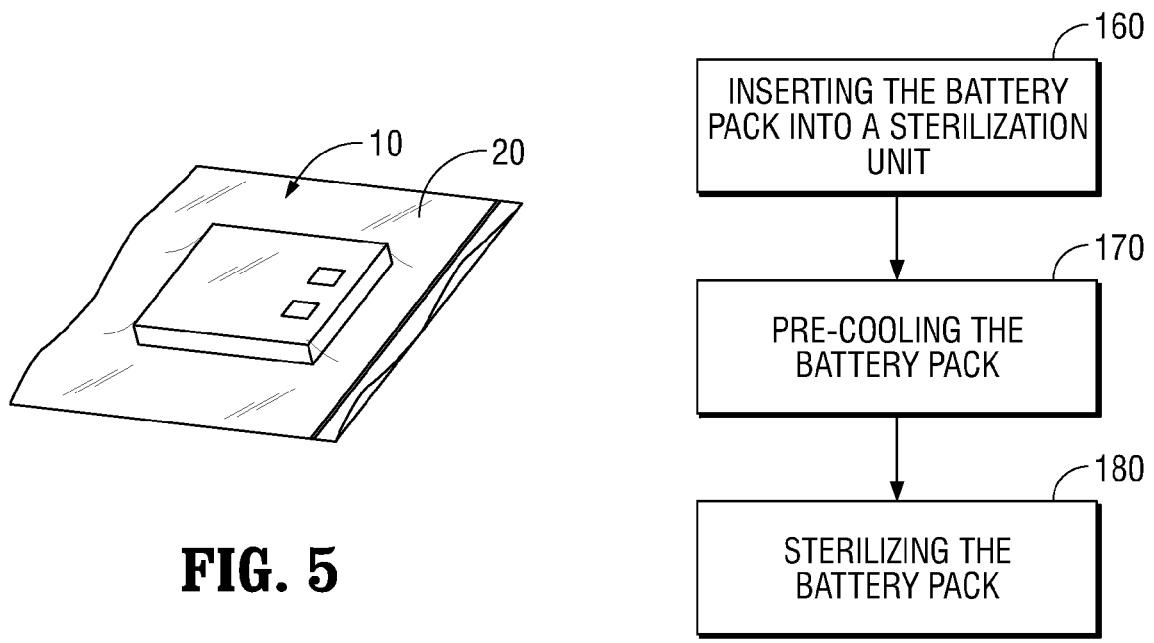
FIG. 5
FIG. 6

PROCESS OF COOLING SURGICAL DEVICE BATTERY BEFORE OR DURING HIGH TEMPERATURE STERILIZATION

CROSS REFERENCE TO RELATED APPLICATION

The present application is a divisional application of U.S. patent application Ser. No. 13/436,107, filed on Mar. 30, 2012, which claims the benefit of and priority to U.S. Provisional Application Ser. No. 61/469,543, filed on Mar. 30, 2011, entitled "PROCESS OF COOLING SURGICAL DEVICE BATTERY BEFORE OR DURING HIGH TEMPERATURE STERILIZATION", the entirety of which are hereby incorporated by reference herein for all purposes.

BACKGROUND

1. Technical Field

The present disclosure is directed to a system and method for autoclaving a battery pack, and more particularly, to maintaining the inner battery cell (or cells) of the battery pack at a lower, safer temperature while still sterilizing the remainder of the device.

2. Background of Related Art

Portable surgical instruments are known in the medical arts. Portable surgical instruments overcome some of the drawbacks that are typically associated with surgical instruments that draw power from electrical outlets. That is, outlet driven surgical instruments utilize power cords that may create tripping and/or entanglement hazards in an operating room environment.

Typically, the portable surgical instrument includes a battery or battery assembly that is configured to removably couple or "latch" to the portable surgical instrument. In an ideal scenario, the battery or battery assembly remains coupled or "latched" to the portable surgical instrument during the entirety of the surgical procedure. However, in certain instances, the battery or battery assembly has to be uncoupled or "unlatched" from the portable surgical instrument during the surgical procedure. As can be appreciated, removable batteries or battery assemblies that are configured to quickly and easily couple or latch to a handpiece of the portable surgical instrument may prove advantageous in the surgical environment. For example, the battery or battery assembly may have to be unlatched from the surgical instrument for sterilization (or re-sterilization), charging (or recharging), replacement, etc.

It is desirable to re-sterilize a rechargeable battery pack using the most prevalent sterilization means available in a hospital, namely, by using an autoclave. Yet this high temperature method is above the temperature limits of currently available rechargeable battery cells. At such high temperatures batteries may become damaged during the autoclaving procedure.

SUMMARY

A dual-mode autoclave for sterilizing a battery is disclosed including a controller and an environmental system in operative communication with the controller and configured sterilize a battery contained within the dual-mode autoclave in response to a command from the controller. The environmental system is configured to reduce a temperature of the battery to a first, pre-cooled temperature during a first operational phase, and configured to increase the temperature of the battery to a second, autoclaving temperature during a second operational phase.

In an aspect of the present disclosure, the dual-mode autoclave includes a sensor operatively associated with the controller and configured to sense at least one parameter of the battery.

In an aspect of the present disclosure, the battery includes an identifier indicative of the at least one parameter of the battery, the sensor configured to sense the identifier and to determine the at least one parameter of the battery from the identifier.

In an aspect of the present disclosure, the pre-cooled temperature and the autoclaving temperature are determined at least in part by the at least one parameter of the battery.

In an aspect of the present disclosure, the first, pre-cooled temperature is equal to or less than about $-12°$ C.

In an aspect of the present disclosure, the second, autoclaving temperature is equal to or greater than about $121°$ C.

A method for sterilizing a battery is disclosed including inserting a battery into a dual-mode autoclave, pre-cooling the battery to a pre-cooled temperature during a first operational phase of the dual-mode autoclave, and heat autoclaving the battery to an autoclaving temperature during a second operational phase of the dual-mode autoclave.

In an aspect of the present disclosure, the method further includes receiving a user input at a user interface of the dual-mode autoclave and executing at least one of the first operational phase or second operational phase in response to the user input.

In an aspect of the present disclosure, a single user input executes the first operational phase followed by the second operational phase.

In an aspect of the present disclosure, the method further includes sensing at least one parameter of the battery and adjusting at least one of the pre-cooled temperature or the autoclaving temperature based on the sensed at least one parameter of the battery.

A sterilization system is disclosed including a battery having an active cooling system and an autoclave including a coolant supply system. The coolant supply system is configured to operatively couple to the active cooling system of the battery when the battery is disposed within the autoclave. The active cooling system is configured to maintain the battery at a reduced temperature during a heat autoclaving cycle.

In an aspect of the present disclosure, the autoclave includes a battery charging device configured to operatively engage the battery in electrical communication when the battery is disposed within the autoclave. The battery charging device is configured to at least partially recharge the battery during the heat autoclaving cycle.

In an aspect of the present disclosure, the battery charging device includes at least one contact configured to electrically engage a contact of the battery.

In an aspect of the present disclosure, the battery includes an inner battery cell. The active cooling system is disposed in thermal communication with the inner battery cell and configured to reduce the temperature of the inner battery cell during the heat autoclaving cycle.

In an aspect of the present disclosure, the battery includes at least one peltier module in operable communication with the controller and disposed at least partially between the inner battery cell and the active cooling system, the at least one peltier module being activatable by the controller to increase heat transfer from the inner battery cell to the active cooling system during the heat autoclaving cycle.

In an aspect of the present disclosure, the autoclave includes a receptacle configured to receive the battery therein. The receptacle is configured to couple the coolant supply system of the autoclave with the active cooling system of the battery in a substantially fluid-sealed manner.

In an aspect of the present disclosure, the battery includes a temperature sensor configured to sense a temperature of the battery. The temperature sensor is disposed in operative communication with the autoclave.

In an aspect of the present disclosure, the temperature sensor is configured to transmit a temperature signal to the autoclave when the temperature of the battery reaches a predetermined threshold and the autoclave configured to activate the coolant supply system when temperature signal is received.

In an aspect of the present disclosure, the coolant supply system is configured to continuously supply the active cooling system of the battery with the at least one of a coolant or a refrigerant.

In an aspect of the present disclosure, the coolant supply system of the autoclave and the active cooling system of the battery are configured to maintain the inner battery cell below a temperature of about 60° C.

It is contemplated that any of the above aspects and embodiments may be combined without departing from the scope of the present disclosure.

As used herein, the term "battery pack" and "battery" are used interchangeably and generally refer to a removable power source including one or more battery cells.

BRIEF DESCRIPTION OF THE DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIG. 1A is a perspective view of an embodiment of a battery in accordance with the present disclosure;

FIG. 1B is a side, cross-sectional view of the battery of FIG. 1 taken along section line 1B-1B;

FIG. 2 is a perspective view of an embodiment of a dual-mode autoclave in accordance with the present disclosure, illustrating a pre-cooling cycle;

FIG. 3 is a perspective view of the dual-mode autoclave of FIG. 2, illustrating a heat autoclaving cycle;

FIG. 4 is a schematic view of the components of the dual-mode autoclave of FIG. 2;

FIG. 5 is a perspective view of the battery of FIG. 1, illustrating the battery disposed in a sterilization pouch;

FIG. 6 is a block diagram of a method of sterilization in accordance with the present disclosure;

DETAILED DESCRIPTION OF EMBODIMENTS

Figure 7A:
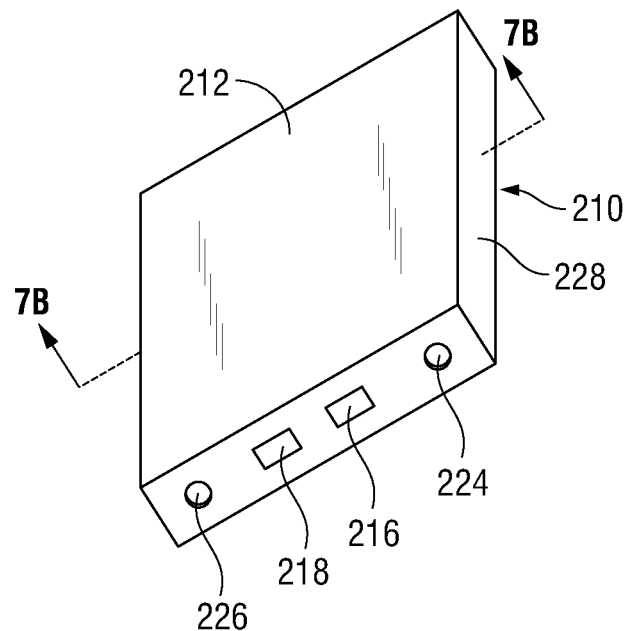
FIG. 7A is a perspective view of an embodiment of a battery in accordance with the present disclosure.

Embodiments of the presently disclosed system will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

The present disclosure is directed to a system and method for autoclaving a battery pack, and more particularly, to maintaining an inner battery cell (or cells) of the battery pack at a lower, safer temperature while sterilizing the rest of the battery pack. The disclosed method includes cooling the battery pack before or during sterilization. Pre-cooling of the battery pack may include freezing the battery pack to very low temperatures, e.g., at or below about −12° C. This results in liquid components of the battery pack gaining added heat of fusion energy absorption. Thermally insulating the battery pack may also reduce heat transfer to the inner battery cells of the battery pack and may be used in conjunction with cooling to prevent high temperatures.

With reference now to FIGS. 1A and 1B, there is disclosed a battery pack 10 for use with a cordless surgical instrument (not shown). An example of a suitable cordless surgical instrument is disclosed in co-pending U.S. patent applicant Ser. No. 13/312,299, filed on Dec. 6, 2011, entitled "PORTABLE SURGICAL INSTRUMENTS", the entirety of which is hereby incorporated by reference herein for all purposes.

Battery pack 10 includes a housing 12 having an inner battery cell 14 and a pair of contacts 16 and 18 on an external surface and in electrical communication with battery cell 14. It is contemplated that more than one inner battery cell 14 may be provided. Inner battery cell 14 may be any suitable kind of battery cell now known or in the future known that is configured for use with a cordless surgical instrument including, for example, without limitation, lithium ion, lithium ion polymer, nickel metal hydride, lead-acid, and nickel cadmium.

Housing 12 of battery pack 10 may include thermal insulation 13 for insulating battery pack 10 and inner battery cell 14 to reduce the heat transferred from the exterior of battery pack 10 to inner battery cell 14 during heat autoclaving.

With reference now to FIGS. 2 and 3, a dual-mode autoclave device 100 is disclosed for use in sterilizing a medical object 110, e.g., battery pack 10. Dual-mode autoclave device 100 is configured for both cooling and heating during a sterilization process. For example, dual-mode autoclave device 100 may include a first operational phase where the medical object 110 is pre-cooled, and a second operational phase where the medical object is heat autoclaved.

With reference now to FIGS. 2-4, dual-mode autoclave device 100 includes a user interface 120 configured to receive a user input and to display a status of dual-mode autoclave device 100. User interface 120 is in operable communication with a controller 130 that is configured to execute a set of program instructions in accordance with a user input received at the user interface 120. For example, upon reception of a user input at user interface 120, controller 130 may execute the first operational phase by commanding an environmental system 140 of the dual-mode autoclave device 100 to pre-cool the medical object 110. Alternatively, upon reception of a user input at user interface 120, controller 130 may execute the second operational phase by commanding the environmental system 140 to heat sterilize the medical object 110, e.g., autoclaving using high pressure and high temperature steam. Environmental system 140 may include a cooling unit 142 and a heating unit 144. It is contemplated that both heat and cooling may be performed by a single unit and that a single user input at the user interface 120 may automatically command controller 130 to execute the first operational phase followed the second operational phase.

User interface 120 includes actuation elements 122, e.g., buttons, knobs, touch screens or other similar elements, and display elements 124 for displaying a status of the dual-mode autoclave device 100 to the user. For example, display elements 124 may display a mode (e.g., idle, first operational phase, or second operational phase), a temperature reading, a pressure reading, a sterilization completion indicator, or other similar status indicators.

With reference now to FIG. 4, dual-mode autoclave device 100 may also include a sensor 150 in operative communication with controller 130 and configured to automatically sense an attribute of the medical object 110 to be sterilized. For example, sensor 150 may sense the type of medical object 110 to be sterilized or the number of medical objects 110 disposed within dual-mode autoclave device 100 for sterilization. The controller 130 receives the sensed information from sensor 150 and may automatically tailor the cooling/heating times and temperature profiles of the first and second operational phases to achieve a desired (e.g., optimal) sterilization result based on the sensed type or quantity. Sensor 150 may be configured to sense the medical object type and quantity in a number of different ways. For example, medical object 110 may be disposed in electrical communication with sensor 150 when disposed within dual-mode autoclave device 100 such that sensor 150 can sense an electrical property of the medical object 110. Sensor 150 may include an RFID interrogator and each medical object 110 may include a unique RFID tag such that sensor 150 may read the RFID tags to determine the type and quantity of medical objects 110, or sensor 150 may include an optical reader and medical object 110 may include a unique barcode or other optical code to be read by sensor 150. Sensor 150 may also be configured to sense the current temperature within dual-mode autoclave device 100 for displaying on user interface 120 or for providing temperature feedback to controller 130 and environmental system 140.

With reference now to FIG. 5, battery pack 10 may be placed into a sterilization pouch 20 after sterilization is complete to maintain battery pack 10 in a sterilized condition during transport to the operating room. Alternatively, battery pack 10 may be placed into sterilization pouch 20 prior to sterilization and both battery pack 10 and sterilization pouch 20 may be placed into dual-mode autoclave device 100 for sterilization.

With reference now to FIG. 6, a method of sterilizing battery pack 10 is disclosed. During step 160, the user or operator inserts one or more medical objects 110, e.g., battery packs 10, into dual-mode autoclave device 100 prior to sterilization. As discussed above, battery pack 10 may be inserted into sterilization pouch 20 prior to insertion into dual-mode autoclave device 100 such that both battery pack 10 and sterilization pouch 20 are sterilized. Once battery pack 10 has been inserted into dual-mode autoclave device 100, sensor 150 may sense the type and/or quantity of battery pack 10 as described above. Sensor 150 may sense the type and/or quantity in response to a user input at user interface 120 commanding controller 130 to execute one of the first operational phase (pre-cooling) and the second operational phase (heat autoclaving). Alternatively, sensor 150 may sense the type and/or quantity as soon as the dual-mode autoclave device 100 is sealed with battery pack 10 inside.

During step 170, controller 130 executes the first operational phase to pre-cool battery pack 10. It is contemplated that controller 130 may adjust the temperature and duration of the first operational phase based on the type and quantity sensed by sensor 150. For example, if the type of battery pack 10 sensed by sensor 150 includes thermal insulation, the duration of the first operational phase may be increased to allow inner battery cell 14 to achieve the desired pre-cooled temperature. During the first operational phase, battery pack 10 may be cooled to a very low or freezing temperature, for example, about −12° C. or lower.

During step 180, controller 130 executes the second operational phase to heat autoclave battery pack 10 using high temperature and high pressure steam, for example, about 121° C. or higher. Because battery pack 10 was pre-cooled during step 170, inner battery cell 14 has an increased heat of fusion energy absorption thereby allowing inner battery cell 14 to be maintained in a safe or cool state even during heat autoclaving. For example, in the case of a Lithium-Ion battery, inner battery cell 14 may be maintained at a temperature less than about 60° C., the temperature at which significant degradation or damage occurs. This prevents unnecessary damage to inner battery cell 14 due to overheating and extends the longevity of inner battery cell 14.

As discussed above, it is contemplated that a single user input at user interface 120 may command controller 130 to first perform step 170 and subsequently perform step 180. It is further contemplated that each of steps 170 and 180 may be individually activated by a user. For example, where medical object 110 is not a battery pack 10 or other similar object that does not degrade or otherwise damage under high heat, no pre-cooling may be necessary. Thus, the sterilization cycle time may be reduced by only selecting the second operational phase (e.g., heat autoclaving). It is also contemplated that user interface 120 may allow the user to select from a series of pre-set cooling/heating time and temperature profiles without the use of sensor 150.

Figure 7B:
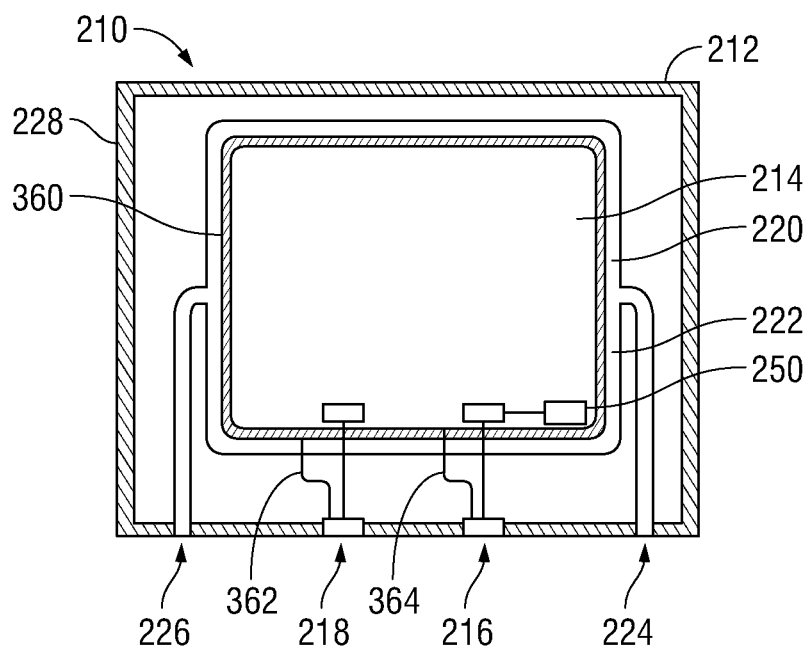
FIG. 7B is a side, cross-sectional view of the battery of FIG. 7A taken along section line 7B-7B.

In another embodiment, with reference now to FIGS. 7A and 7B, active cooling or refrigeration of a battery pack 210 during sterilization may also be used to prevent an inner battery cell 214 of the battery pack 210 from reaching high temperatures. In this embodiment, a battery pack 210 is disclosed including a housing 212 having contacts 216 and 218 disposed thereon. An inner battery cell 214 is disposed within housing 212 and in electrical communication with contacts 216 and 218. Housing 212 further includes an active cooling system 220, e.g., a coolant channel 222, which supplies a refrigerant or coolant to the interior of housing 212 during heat autoclaving, e.g., high pressure and high temperature steam autoclaving. Coolant channel 222 surrounds at least a portion of inner battery cell 214 and includes inlet and outlet openings 224, 226 on a surface of housing 212 for receiving and returning, respectively, a coolant or refrigerant fluid. Active cooling system 220 allows inner battery cell 214 of battery pack 210 to be cooled while an external surface 228 of housing 212 is sterilized through heat autoclaving. For example, active cooling system 220 assists in maintaining inner battery cell 214 below 121° C., the temperature typically used for high pressure and high temperature steam autoclaving. For example, in the case of a Lithium-Ion battery, the active cooling system 220 may maintain inner battery cell 214 at a temperature less than about 60° C., the temperature at which significant degradation or damage occurs.

Figure 8:
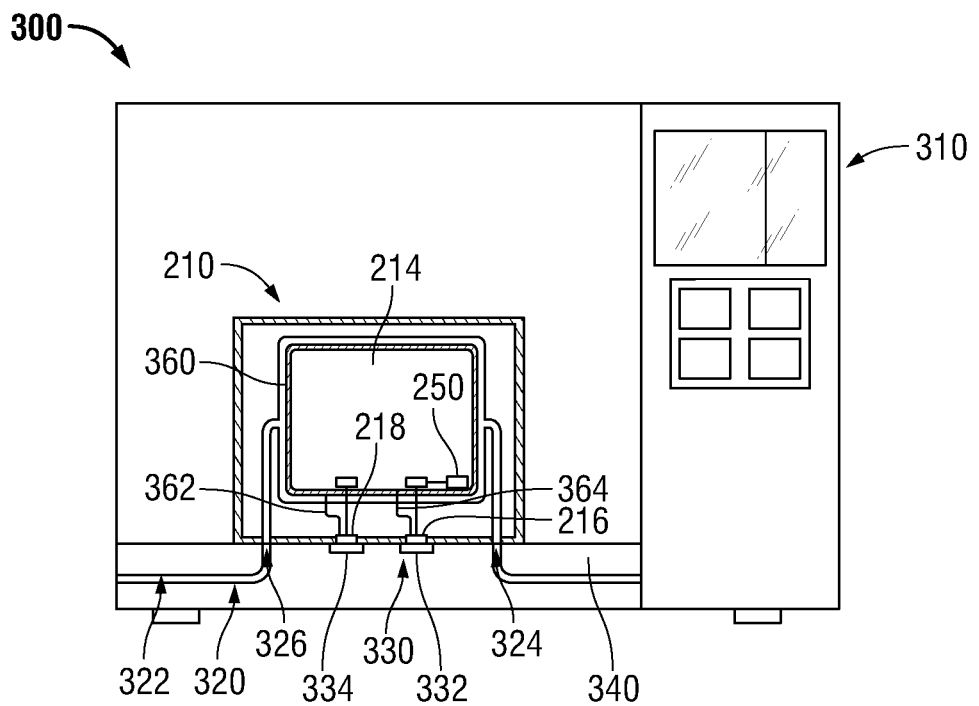
FIG. 8 is a side, cross-sectional view of an embodiment of an autoclave in accordance with the present disclosure.
Figure 9:
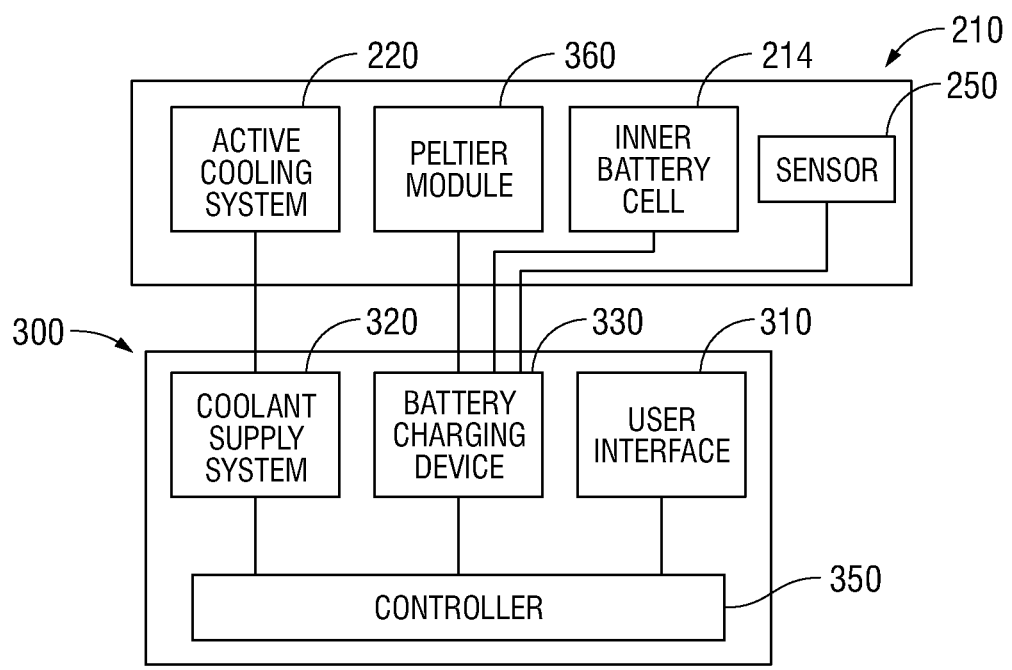
FIG. 9 is a schematic view of the components of the autoclave of FIG. 8.

With reference now to FIGS. 8 and 9, an autoclave device 300 includes a user interface 310 configured to receive a user input from a user and a controller 350 in operative communication with user interface 310 and configured to control the operation of autoclave device 300 in response to the user input. The controller 350 may additionally or alternatively automatically control the operation of autoclave device 300 without a user input. The user interface 310 is also configured to display a status of autoclave device 300 thereon similar to user interface 120 above.

Autoclave device 300 further includes a coolant supply system 320 in operative communication with controller 350. Coolant supply system 320 includes a coolant supply channel 322 having openings 324, 326 configured to selectively couple to inlet and outlet openings 224, 226 of battery pack 210 in a substantially fluid-sealed manner. Controller 350 is configured to command coolant supply system 320 to supply coolant, refrigerant, or other fluids from coolant supply channel 322 to coolant channel 222 of battery pack 210 during heat autoclaving. Coolant supply system 320 may be self-contained within autoclave device 300 or may receive coolant, refrigerant, or other fluids from an external source. Coolant supply system 320 may include pumps (not shown) or other similar devices configured to circulate fluid through coolant supply channel 322 and into battery pack 210.

Autoclave device 300 may also include a battery charging device 330 in operative communication with controller 350. Battery charging device 330 includes contacts 332, 334 configured to selectively engage contacts 216, 218 of battery pack 210 such that battery charging device 330 is in electrical communication with inner battery cell 214. This allows inner battery cell 214 to be recharged during the heat autoclave cycle.

Battery pack 210 may be received by a receptacle 340 of autoclave device 300 which couples battery charging device 330 and/or the coolant supply system 320 to battery pack 210. Controller 350 is configured to activate a charging cycle of battery charging device 330 and/or a cooling cycle of coolant supply system 320.

Battery pack 210 may include a temperature sensor 250 that senses a temperature of internal battery cell 214 and provides a temperature signal to battery charging device 330, and/or to controller 350. If the temperature of internal battery cell 214 exceeds a predetermined value, the controller 350 commands the coolant supply system 320 to circulate a coolant, refrigerant, or other similar liquid through coolant supply channel 322 of autoclave device 300 and coolant channel 222 of battery pack 210 to maintain internal battery cell 214 at a desired temperature. During autoclaving, coolant or refrigerant may be circulated through coolant channel 222 of battery pack 210 continuously, or alternatively, in response to a temperature signal indicative of a high internal battery cell 214 temperature.

Battery pack 210 may also include one or more peltier modules 360 in operable communication with battery charging unit 330 and/or controller 350. Peltier modules 360 may be activated to increase heat transfer from internal battery cell 214 to the coolant/refrigerant being circulated through coolant channel 222. The peltier module 360 may be powered by internal battery cell 214, battery charging unit 330, or by an external source of power (e.g., supplied by a power unit within the autoclave) via wires 362, 364.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A sterilization system, comprising:
a battery including an active cooling system; and
an autoclave including a coolant supply system, the coolant supply system configured to operatively couple to the active cooling system of the battery when the battery is disposed within the autoclave, the active cooling system configured to maintain the battery at a reduced temperature during a heat autoclaving cycle.

2. The sterilization system according to claim 1, wherein the autoclave includes a battery charging device configured to operatively engage the battery in electrical communication when the battery is disposed within the autoclave, the battery charging device configured to at least partially recharge the battery during the heat autoclaving cycle.

3. The sterilization system according to claim 2, wherein the battery charging device includes at least one contact configured to electrically engage a contact of the battery.

4. The sterilization system according to claim 2, wherein the coolant supply system is configured to continuously supply the active cooling system of the battery with a fluid.

5. The sterilization system according to claim 1, wherein the battery includes an inner battery cell, the active cooling system being disposed in thermal communication with the inner battery cell and configured to reduce the temperature of the inner battery cell during the heat autoclaving cycle.

6. The sterilization system according to claim 5, wherein the battery includes at least one peltier module in operable communication with the controller and disposed at least partially between the inner battery cell and the active cooling system, the at least one peltier module being activatable by the controller to increase heat transfer from the inner battery cell to the active cooling system during the heat autoclaving cycle.

7. The sterilization system according to claim 6, wherein the coolant supply system of the autoclave and the active cooling system of the battery are configured to maintain the inner battery cell below a temperature of about 60° C.

8. The sterilization system according to claim 1, wherein the autoclave includes a receptacle configured to receive the battery therein, the receptacle configured to couple the coolant supply system of the autoclave with the active cooling system of the battery in a substantially fluid-sealed manner.

9. The sterilization system according to claim 1, wherein the battery includes a temperature sensor configured to sense a temperature of the battery, the temperature sensor being disposed in operative communication with the autoclave.

10. The sterilization system according to claim 9, wherein the temperature sensor is configured to transmit a temperature signal to the autoclave when the temperature of the battery reaches a pre-determined threshold, the autoclave configured to activate the coolant supply system when temperature signal is received.

11. A sterilization system, comprising:
a battery pack housing at least one battery cell, the battery pack defining at least one internal fluid channel and at least one first port in communication with the at least one internal cooling channel; and
a sterilization device configured to sterilize the battery pack, the sterilization device including at least one second port configured to operably couple to the at least one first port of the battery pack for circulating fluid through the at least one internal fluid channel of the battery pack.

12. The sterilization system according to claim 11, wherein the sterilization device is an autoclave configured to receive the battery pack.

13. The sterilization system according to claim 11, wherein the sterilization device further includes a battery charging device configured to operatively engage the battery pack to enable at least partial recharging of the at least one battery cell during sterilization of the battery pack.

14. The sterilization system according to claim 13, wherein the battery charging device includes at least one contact configured to electrically engage a corresponding contact disposed on the battery pack.

15. The sterilization system according to claim 11, wherein the circulation of fluid through the at least one internal fluid channel of the battery pack cools the at least one battery cell during sterilization of the battery pack.

16. The sterilization system according to claim 11, wherein the sterilization device further includes a receptacle configured to receive the battery pack therein, the receptacle configured to connect to a fluid source for circulating fluid through the at least one internal fluid channel of the battery pack.

17. The sterilization system according to claim 11, wherein the battery pack further includes an internal temperature sensor configured to sense a temperature of the at least one battery cell.

18. The sterilization system according to claim 17, wherein the temperature sensor is operatively coupled to the sterilization device and configured to transmit a temperature signal to the sterilization device, the sterilization device configured to control the circulation of fluid through the at least one internal fluid channel of the battery pack in accordance with the received temperature signal.

* * * * *